United States Patent
Bergström et al.

(10) Patent No.: US 6,472,576 B1
(45) Date of Patent: Oct. 29, 2002

(54) PROCESS FOR PREPARING 2,6-DIMETHYLNAPHTHALENE

(75) Inventors: Christer Bergström; Marita Niemelä, both of Espoo (FI)

(73) Assignee: Optatech Corporation, Espoo (FI)

( * ) Notice: Subject to any disclaimer, the term of this patent is extended or adjusted under 35 U.S.C. 154(b) by 0 days.

(21) Appl. No.: 09/857,277

(22) PCT Filed: Dec. 2, 1999

(86) PCT No.: PCT/FI99/01001

§ 371 (c)(1),
(2), (4) Date: Jun. 1, 2001

(87) PCT Pub. No.: WO00/34212

PCT Pub. Date: Jun. 15, 2000

(30) Foreign Application Priority Data

Dec. 4, 1998 (FI) .................................................. 982630

(51) Int. Cl.⁷ .............................. C07C 5/24; C07C 5/00
(52) U.S. Cl. ....................................... 585/411; 585/410
(58) Field of Search ................................. 585/410, 411, 585/414, 420

(56) References Cited

U.S. PATENT DOCUMENTS 4,447,665 A  5/1984  Wennerberg ................. 585/379

FOREIGN PATENT DOCUMENTS

| | | |
|---|---|---|
| EP | 0362507 | 4/1990 |
| EP | 0586819 | 3/1994 |
| GB | 1448136 | 9/1976 |
| WO | WO 97/30012 | 8/1997 |

*Primary Examiner*—Thuan D. Dang
(74) *Attorney, Agent, or Firm*—Cohen, Pontani, Lieberman & Pavane

(57) ABSTRACT

A process for producing 2,6-dimethylnapthalene from 1-(p-tolyl)-2-methylbutane, 1-(p-tolyl)-2-methylbutene or a mixture thereof by dehydrocyclization in the presence of a catalyst, comprising using non-acidic activated carbon as a catalyst.

16 Claims, No Drawings

PROCESS FOR PREPARING 2,6-DIMETHYLNAPHTHALENE

BACKGROUND OF THE INVENTION

1. Field of Invention

The present invention relates generally to the production of dimethylnapthalene. In particular, it relates to a process for preparing 2,6-dimethylnapthalene by dehydrogenation and cyclization of 1-(p-tolyl)-2-methylbutane or 1-(p-tolyl)-2-methylbutene) in the presence of a catalyst.

2. Description of Related Art 2,6-dimethylnapthalene (in the following also abbreviated "2,6-DMN") is a desirable raw material required for the production of 2,6-naphthalene dicarboxylic acid. Said carboxylic acid can be obtained by oxidation using known oxidation processes (see for example U.S. Pat. No. 5,183,933, Harper et al.). 2,6-naphthalene dicarboxylic acid is an important intermediate in the manufacture of speciality polymers, such as poly(ethylene naphthalate) (PEN) and liquid crystal polymers. The cost of PEN depends strongly on the price of 2,6-naphthalene dicarboxylic acid and, thus, on the price of its raw material 2,6-DMN. Therefore, for the economics of the process, it is essential that 2,6-DMN of high purity and good quality is selectively produced with an inexpensive process.

At present, 2,6-DMN is prepared by a multistep synthesis which starts by alkylation of o-, m- or p-xylene with 1- or 2-butene or, preferably, butadiene to yield 5-(o-, m-, or p-tolyl)-pent-1 (or -2-)-ane or -ene, which is subsequently converted to 1,5-, 1,6-, 2,5- or 2,6- dimethyltetralin. The tetralins are dehydrogenated to the corresponding dimethylnaphthalenes, and isomerized to yield 2,6-dimethylnapthalene (2,6-DMN). This prior art is discussed by Sikkenga et al. who disclose multi-step liquid phase syntheses for the cyclisation of specific alkenyl benzenes to one or more specific dimethyl tetralins in the presence of suitable solid acid cyclisation catalysts, such as acidic crystalline zeolites, followed by dehydrogenation to corresponding dimethylnapthalene(s) and isomerization of the resulting dimethylnaphthalenes to the desired specific dimethylnapthalene (cf. U.S. Pat. Nos. 5,073,670, 5,401,892, 5,118,892, 5,012,024 and 5,030,781 and Published PCT Application WO 89/12 612.

A problem associated with most of the prior art methods is the utilisation of 1-(o-, m-, or p-tolyl) pent-1-or-2-ene type straight-chained alkenylated compounds as a starting material, which results in the use of an acidic cyclisation catalyst. Consequently, after dehydrogenation the product stream contains several dimethylnaphthalenes, and a subsequent step of isomerisation and/or separation is required. It has therefore been highly desired to improve the selectivity of the cyclisation step in the aforesaid multistep processes, and even more desirable also to decrease the number of necessary process steps in order to achieve a more economic performance.

To that end, EP 0 430 714 B1 (Mitsubishi Gas Chemicals) suggests a process for producing 2,6-dimethylnapthalene by subjecting 2-methyl-1-(p-tolyl)-butene, 2-methyl-1-(p-tolyl)-butane or a mixture of thereof to cyclization and dehydrogenation in the presence of (a) a catalyst comprising lead oxide and/or indium oxide and aluminum oxide; (b) a catalyst comprising lead oxide and/or indium oxide, aluminum oxide and alkali metal oxide and/or alkaline earth metal oxide; (c) a catalyst comprising lead oxide and/or indium oxide, aluminum oxide and at least one oxide of the metals: iron, tin antimony, chromium, zinc, vanadium, nickel or cobalt; or (d) a catalyst comprising lead oxide and/or indium oxide, aluminum oxide, an oxide of iron, tin antimony, chromium, zinc, vanadium, nickel and/or cobalt and an oxide of alkali metal and/or alkaline earth metal. A later patent, EP 0 546 266 B1, discloses the use of a catalyst comprising a platinum component and at least one component selected from alkali metals or alkaline earth metals and supported on alumina. Finally , EP 0 557 722 B1 discloses the use of a catalyst which comprises palladium, alkali metal compound and aluminum oxide. In the catalyst, 0.05–20 wt-% of palladium together with 0.1–20 wt-% of alkali metal is supported on alumina, and the catalyst is used in cyclisation dehydrogenation reaction at 350–700 ° C. in the presence of a solvent/diluent such as toluene, benzene, steam or the like to suppress side reactions such as polymerisation.

Although the selectivity of the process has been somewhat increased by the art suggested in above-mentioned patents, further improvement is still required. There is also a need for an inexpensive process which provides for easy separation of by-products. In particular the formation of alkyl-substituted indanes and indenes should be minimized.

SUMMARY OF THE INVENTION

It is an object of the present invention to provide a process for manufacturing 2,6-DMN with improved yield and selectivity by cyclisation of an alkenylbenzene (alkyl-benzene), 1-(p-tolyl)-2-methylbutene (1-(p-tolyl)-2-methylbutane).

It is a second object of the present invention to provide a novel catalyst which is suitable for use in, e.g., dehydrocyclisation reactions.

It is a third object of the present invention to provide a new use of activated carbon.

These and other objects, together with the advantages thereof over known processes, which shall become apparent from the specification which follows, are accomplished by the invention as hereinafter described and claimed.

The present invention is based on the finding that a key feature in selectivity enhancement of dehydrocyclisation reactions is the composition of the heterogeneous catalyst. By neutralisation of acid sites present on supports of catalysts for dehydrocyclisation it becomes possible to suppress unwanted cracking reactions as well as undesired acid catalysed condensation reactions. Surprisingly, it has further been found that high activity and good selectivity is obtained with inexpensive catalysts consisting essentially of activated carbon. Thus, such materials which traditionally have been used as supports for noble metal catalyst have turned out to possess high activity for dehydrocyclisation as such (without any catalytically active metal species). The activity of the activated carbon is further increased when it is neutralized or otherwise modified so as to produce non-acidic carbon. When a noble metal is deposited on such a support a non-acidic noble metal catalyst is obtained on which the reaction proceeds only on the metallic sites.

The present invention also provides a novel kind of catalyst comprising chromium deposited on an active carbon support. This catalyst is useful for dehydrocyclisation reactions.

The present invention provides considerable advantages. Thus, the selectivity is improved compared to that of bifunctional systems, wherein two types of active sites, the metallic and acidic, operate simultaneously offering diverse reaction routes. Activated carbon is an inexpensive catalyst that is readily available. Furthermore, it has been found that advantageous results are obtained by employing a highly dispersed catalyst for ring closure in dehydrocyclisation. Monofunctional non-acidic well-dispersed noble metal catalysts are therefore suitable for dehydrocyclisation of a specific methyl-alkenylbenzene, such as 1-(p-tolyl)-2-methylbutene, to form 2,6-DMN in one step.

The present process provides for easy separation of by-products and the formation of alkyl-substituted indanes and indenes is minimized.

DETAILED DESCRIPTION OF THE INVENTION

The present invention primarily relates to an improved method for manufacturing 2,6-DMN in one step instead of by a multistep synthesis, that is, to convert alkenylbenzene (alkylbenzene), 1-(p-tolyl)-2-methylbutene (1-(p-tolyl)-2-methylbutane) by dehydrocyclisation to 2,6-DMN. The catalysts described herein can, however, also be employed in conventional multistep-synthesis methods, although that application is not particularly preferred.

The present one-step reaction is carried out in the presence of a solid dehydrocyclisation catalyst comprising an essentially neutral support at an elevated temperature and ambient pressure in gaseous phase using a gas mixture as a carrier gas.

The catalyst can comprise activated carbon as such or a noble metal component, e.g. Rh or Pt, or a transition metal component, e.g. Cr, deposited on the support. In the presence of an essentially neutral catalyst system the reaction proceeds on the metal sites of the catalyst.

Experimental results obtained in connection with the present invention surprisingly indicate that activated carbon, also called activated charcoal and abbreviated "AC", exhibits high activity for the reaction of 1-(p-tolyl)-2-me-butene. The activated carbon can comprise a product of a quality conventionally suitable for use as a support for noble metal catalysts.

Three parameters are of particular importance for characterizing the carbon materials, viz. porosity, ash content/purity and acidity/alkalinity.

The activated carbons used in the present invention are porous, and the pore sizes depend on carbon type. Pores above 50 nm in width are generally called "macropores", whereas pores between 2 and 50 nm are "mesopores", and pores below 2 nm in width are "micropores". It should be noted that each of the carbon types comprises a wide range of pores with various sizes. However, according to a specific embodiment, it is preferred to use activated carbons in which at least 7% of the pores are mesopores or macropores. In particular, the fraction of meso- and macropores (2 nm<$d_{pore}$<50 nm and $d_{pore}$>50 nm) should be about 10 to 60%. It appears that the mass transfer of the reactants as well as the reaction of rather large compounds is significantly restricted in highly microporous materials. It is also possible that some of the pores of microporous materials become blocked when metal species are deposited on the surface thereof, whereas more mesoporous materials are better capable of retaining their pores open., but this is only a suggestion.

As mentioned above, the ash content of activated carbons also varies, and according to a specific embodiment it is preferred to use an activated carbon support having a low ash content. In particular, ash contents of less than 2% and preferably less than 1% are preferred. Low-ash carbons generally contain only small amounts of impurities such as sulphur and chlorine. A particularly preferred embodiment comprises a combination of low ash content (<1%) and a mesoporous structure (fraction of meso- and macropores being larger than 15%).

Activated charcoal supports can also be characterized by their pH value as acidic, neutral or alkaline materials. Although the acidic carbons are active by themselves, according to the present invention, the performance of such a product is detrimentally influenced by its acidic nature and can be improved by decreasing the acidity.

According to a preferred embodiment, the acidity of the activated carbon is decreased by thermally decomposing the surface groups responsible for it. Thus, an acidic activated carbon can be subjected to a pretreatment carried out at an elevated temperature. Preferably the activated carbon is treated at temperatures in the range of 400 to 1000 ° C. The test results discussed below (cf. Table 5) indicate that the pretreated supports exhibited similar overall high activity for the reaction of 1-(p-tolyl)-2-me-butene as the support of example 19. In regard to the formation of 2,6-DMN, the selectivity of a pretreated acidic activated carbon support (AC(T)) was significantly better than that of the non-treated AC(T) support. Thus, a high temperature pretreatment eliminates acid sites from the surface and increases selectivity.

Aforesaid acidic sites can also be neutralised by using a metal, such as a metal of Group 1 to 4 and/or a metal of any of Groups 11 to 13. In particular, the catalyst can be neutralised with a suitable alkali metal, such as lithium, sodium or potassium. Thus, as evidenced by the examples below, in which acidic and neutral activated carbons were used as supports of rhodium catalysts, the neutralization of acidic sites on the surface of the carbon with potassium increases the selectivity of the catalysts. By contrast, for an activated carbon having an alkaline surface, no influence on the selectivity could be obtained.

It should be pointed out that the neutralization of the activated carbon by the metals can take place indirectly (=catalyst modification), if the metal species attach to the acidic sites of the carbon catalyst and thus changes the acidic character of the carbon. For the purpose of the present invention a carbon catalyst modified in the above manner is also called a neutralized or neutral carbon.

The neutral activated carbons can be used as supports for noble metal catalysts. The noble metal can be any noble metal having an activity in the present reaction, including noble Group VIII metals. Particularly preferred metals are rhodium, palladium and platinum. The noble metal can be deposited on the surface of the support by methods known per se, e.g. by impregnating or wetting the support with a solution or dispersion of a suitable metal or metal salt. The water or solvent is then removed and the dried material is optionally reduced to release the metal. The concentration of the noble metal is typically 0.01 to 50 wt-%, preferably about 0.1 to 20 wt-% and the metal particles are about 0.1 to 100 nm, preferably about 1 to 30 nm in diameter, in particular about 1 to 10 nm.

The selectivity of supported noble metal catalysts can be further improved by increasing the dispersion of the catalytically active species on the surface of the supports. It appears that meso- and macroporous activated carbon supports provide a better dispersion than microporous supports. A preferred embodiment comprises using a mesoporous activated carbon having a large number of surface binding sites, e.g. comprising acid groups. By using a support having many surface binding sites, the dispersion of the metal can be improved and the formation of aggregates reduced. After the deposition of the metal, the remaining acidic sites are then neutralized.

The benefial (neutralizing) influence of alkali metals was already discussed above. The alkali metal will work as promoter of the catalysts, and contribute to the activity thereof.

It is also possible to promote supported noble metal catalysts with ions of alkaline earth metals, such as magnesium, barium, calcium, or with ions of transition metals, such as copper, zinc, zirconium or cadmium or with boron. Although we do not wish to be bound to any specific theory, it appears that, e.g., zinc ions on the surface of Rh effectively blocks the large ensembles of Rh, and thus results in site isolation of surface Rh.

As the results given below show, in regard to the formation of 2,6-DMN, the selectivity of both the Ba and Zn promoted catalysts were significantly higher than those of their non-promoted counterparts. Thus, all the aforesaid promoters, such as potassium, barium and zinc, are beneficial in terms of the selectivity of the desired product, 2,6-DMN. The present invention also provides a novel heterogeneous catalyst comprising chromium on activated carbon. This catalyst can be used as a dehydrocyclisation catalyst. The catalyst can be prepared by conventional liquid phase or gas phase methods by depositing trivalent chromium ions on the surface of the support from suitable chromium salts. The liquid phase methods include impregnation or wetting of the carbon surface with solutions or dispersions of chromium salts in water or solvents, such as polar solvents.

The chromium loading on the support is 0.1 to 40 wt-%, preferably about 1 to 20 wt-%. The support can be any suitable activated carbon, but based on our experiences particularly preferred are meso- and macroporous activated carbons exhibiting 5 to 50% pores having diameters in the range of 2 to 50 nm and in excess of 50 nm. The surface of the support is neutral(ized).

The new chromium catalysts can be neutralized and promoted as explained above using thermal treatment, alkali metal ions, earth alkaline metal ions and transition metal ions. As the results given below show, the activity of a potassium promoted chromium-on-charcoal catalyst is comparable to that of potassium promoted chromium on alumina catalysts.

The dehydrogenation and cyclisation is carried out by contacting the starting material, such as 1-(p-tolyl)-2-methylbutene with the catalyst at an elevated temperature. The reaction temperature is in the range of 350 to 700 ° C., preferably 450 to 600 ° C. In particular the reaction temperature is below 550 ° C. At these temperatures the starting material will vaporize and the reaction is therefore carried out in gas phase.

Generally, the feed is conducted with a carrier gas into the reactor, in which the catalyst is kept at the reaction temperature. The contact time of the reaction is quite short, typically 3 seconds or less. Hydrogen is often used as a carrier because hydrogen has been found to inhibit fast deactivation of the catalysts. Hydrogen will also reduce the noble metal of the catalyst into elemental form. The problem with hydrogen is, however, that it causes hydrogenation of the starting material. According to the present invention this reaction can be significantly reduced by the use of either a mixture of hydrogen and argon or pure argon or nitrogen as a carrier instead of hydrogen. A particularly preferred embodiment comprises using a catalyst having lower hydrogenation activity than platinum, such as rhodium. Although the activity of rhodium catalysts decreases when the carrier gas is changed from hydrogen to the $H_2$ (3%)/Ar mixture or pure argon, the selectivity of the dehydrocyclisation catalysts is significantly increased when the carrier gas is changed from hydrogen to a said mixture or to pure argon.

Furthermore, a mixture of hydrogen and argon, such as the above ($H_2$ (3%)/Ar mixture) represents a particularly preferred embodiment for catalysts containing rhodium, because it can be used throughout the process, that is for the in situ reduction of the catalyst and as well as for carrier gas.

In summary, the use of a hydrogen/argon mixture will increase 2,6-dimethylnapthalene selectivity and decrease hydrogenation selectivity and/or indanes or indenes selectivity.

The following non-limiting examples illustrate the invention in further detail:

EXAMPLES

COMPARATIVE EXAMPLES

The following catalysts were selected for comparative purposes: a Pt/BaKL catalyst originally developed for aromatisation reactions, alumina supported chromium oxide and chromium catalysts and a bifunctional Pt-Cu/NaY catalyst developed for the liquid phase cyclisation of 5-(o-, m- or p-tolyl)-pent-1 (-or-2)-ene or 5-phenyl-hex-1 (-or-2)-ene materials.

Comparative Example 1

A Pt/BaKL catalyst was prepared by impregnating the KL-zeolite as follows [M. Vaarkamp, J. V. Grondelle, J. T. Miller, D. J. Sajkowski, F. S. Modica, G. S. Lane, B. C. Gates and D. C. Koningsberger, Catal. Lett. 6 (1990) 369]:

The commercial KL-zeolite obtained from Exxon Chemical Europe Inc, Belgium, was ion-exchanged with an excess aqueous Ba-nitrate solution using 5 g of the support and 150 ml 0.3 M $Ba(NO_3)_2$ (overnight). The solid material was washed with distilled water, and dried at 106° C. overnight. The obtained solid was impregnated with 109 mg of $Pt(NH_3)_4(NO_3)_2$ in 6 ml of water. The wet solid was allowed to stand overnight, and it was dried in rotavapor at 60 ° C. The catalyst was calcined at 300° C for 1 h [S. Alerasool and R. D. Gonzales, J. Catal. 124 (1990) 204, and R. D. Gonzales and H. Miura, Catal. Rev. Sci. Eng. 36 (1994) 145], and reduced in situ in hydrogen prior to use, 500° C., 1 h [9].

1 g of the aforesaid catalyst it was loaded into the reactor tube (10 mm) on top of glass wool. The catalyst was reduced in situ under $H_2$ flow of 2l/h at 500° C. for 1 hour and the reaction was commenced by introducing the feed, 1-(p-tolyl)-2-methyl-butene (2.5 ml/h) together with the carrier gas, hydrogen, with a flow rate of 0.5 l/h to the reactor. The reaction temperature was 500° C., and the reaction products were collected into a glass vial during the first hour of time on stream. The products were analysed by a HP gas chromatograph equipped with a Restec column. All the response factors were taken to be equal. [C. Song and S. Kirby, Am. Chem. Soc. Preprint, Div. Petr. Chem., 206th National Meeting, 1993, 784–787]. The results are shown in Table 1. It should be noted that the hydrogenated product, that is 1-(p-tolyl)-2-me-butane, can be recycled, and thus it is included in the ratio (desired products/undesired indenes), that is (2,6-DMN+1-(p-tolyl)-2-me-butane)/indenes.

Comparative Example 2

Commercial $Cr_2O_3/Al_2O_3$ catalyst (Cr-0205 Harshaw) was crushed and sieved to size 0.42–0.84 mm 1 g of the aforesaid catalyst was loaded into the reactor tube (10 mm) on top of glass wool. The catalyst was reduced in situ under $H_2$(3%)/Ar flow of 2l/h at 500° C. for 1 hour and the reaction was commenced by introducing the feed, 1-(p-tolyl)-2-methyl-butene (2.5 ml/h) together with the carrier gas, which contained 3% of hydrogen in argon ($H_2$/Ar) with a flow rate of 0.5l/h to the reactor. The reaction temperature was 500° C., and the reaction products were collected into a glass vial during the first hour of time on stream. The products were analysed by a HP gas chromatograph equipped with a Restec column. All the response factors were taken to be equal [C. Song and S. Kirby, Am. Chem. Soc. Preprint, Div. Petr. Chem., 206th National Meeting, 1993, 784–787]. The results are shown in Table 1.

Comparative Example 3

A K—Cr/$Al_2O_3$ (A) catalyst was prepared as follows:

5 g of the crushed and sieved commercial Cr/$Al_2O_3$ catalyst (Harshaw Cr-0205) with pore volume of 0.29 $cm^3$/g was weighed into a flask, and it was vacuumed at room temperature for 1 hour. The catalyst was impregnated with a solution composed of 1.5 ml water and 0.4418 g $K_2CO_3$, that is 0.25 g K, , i.e., the potassium loading of the catalyst is approx. 5 p%. The impregnated catalyst was allowed to rest for 1 h, and thereafter it was dried at 106° C., and calcined at 500° C. (rate 3° C./min) under air flow for 1 h.

Then, the experimental procedure was carried out as in Comparative Example 2, except for the use of thus prepared K—$Cr_2O_3$/$Al_2O_3$ catalyst instead of the commercial $Cr_2O_3$/$Al_2O_3$.

Comparative Example 4

A K—$Cr_2O_3$/$Al_2O_3$ (B) catalyst was prepared by impregnating a Criterion alumina support with $Cr(NO_3)_3$.$9H_2O$ and $K_2CO_3$ as follows:

5 g of Criterion alumina (particle size 0.5–0.7 mm) was weighed in to a flask, and it was vacuumed for 1 h. The support was impregnated with a solution composed of 2.5 ml of water and 3.421 g of $Cr(NO_3)_3$.$9H_2O$, ie., the metal loading of the catalyst is approx. 8wt % (5 g of support and 0.443 g Cr, that is 0.443:5.443=10 wt %). The impregnated support was allowed to rest for 1 h, and thereafter it was dried in vacuum at room temperature for 1 h. The catalyst was calcined at 500° C. (7° C./min) for 1 h. The calcined catalyst was dried in vacuum for 1 h, and the catalyst was impregnated with a solution composed of 2.5 ml of water and 0.4418 g $K_2CO_3$, that is 0.25 g K (5 wt %). The catalyst was allowed to rest for 1 hour, and thereafter it was dried in vacuum at room temperature for 1 hour. The catalyst was calcined at 500° C. (7° C./min) under air flow for 1 h.

Then, the experimental procedure was carried out as in Comparative Example 2, except for the use of thus prepared K—$Cr_2O_3$/$Al_2O_3$ catalyst instead of the commercial $Cr_2O_3$/$Al_2O_3$.

Comparative Example 5

Comparative Example 5 was carried out as comparative Example 4 except for the use of 1-(p-tolyl)-2-me-butane instead of 1-(p-tolyl)-2-me-butene.

Comparative Example 6

A prior art (Sikkenga et al. WO 89/12612) Pt—Cu/NaY catalyst was prepared as follows:

A solution (S1) was containing 1 wt %/ Pt and 2 wt % Cu was prepared by weighing 2.650 g $H_2(PtCl_6)$.$6H_2O$ and 7.6350 g $Cu(NO_3)_2$.$3H_2O$, and adding water to obtain 100 g. The solution was mixed well. Into 30 g of NaY 15 ml of water and 30 g of solution S1 was added, and the mixture was stirred thoroughly for 30 min. The mixture was transferred into a porcelain crucible and dried at 150° C. for 1 hour. The following day the mixture was calcined by elevating the temperature at a rate of 5° C./min to 500° C. for 4 h. The calcined material was crushed and sieved to approx. 1–2 mm particles.

Then, the experimental procedure was carried out as in Comparative Example 2, except for the use of thus prepared Pt—Cu/NaY catalyst instead of the commercial $Cr_2O_3$/$Al_2O_3$.

Comparative Example 7

A Pt/$SiO_2$ catalyst was prepared on a commercial Grace 432 silica support following the procedures described in the literature [S. Alarasool and R. D. Gonzales, J. Catal. 124 (1990) 204, S. T. Homeyer, and W. M. H. Sachtler, J. Catal., 117 (1989) 91]:

The weighed amount of 10 g of silica support was suspended into distilled water, and the pH of the suspension was adjusted to pH 9 by dropwise addition of 1M $NH_4OH$ solution. A metal precursor solution containing 205 mg of $Pt(NH_3)_4(NO_3)_2$ in 100 ml of water was added dropwise into the suspension to obtain a catalyst with 1 wt-% metal content. The pH of the suspension was again adjusted to the value of 9 by dropwise addition of 1M $NH_4OH$. The suspension was mixed for 12 h, the catalyst was filtered, and washed with distilled water. The catalyst was calcined in air flow for 1 h at 300° C. (turned black), because calcination has been found to increase dispersion.

Then, the experimental procedure was carried out as in Comparative Example 1, except for the use of Pt/$SiO_2$ instead of commercial $Cr_2O_3$/$Al_2O_3$. The results are shown in Table 2.

Comparative Example 8

This example was carried out as Comparative Example 7 except for the use of a $H_2$(3%)/Ar mixture as a carrier gas instead of hydrogen. The results are shown in Table 2.

Comparative Example 9

Comparative Example 9 was carried out as Comparative Example 7 except for the use of argon as a carrier gas instead of hydrogen. The results are shown in Table 2.

The results for (Table 2) the Comparative Examples 8 and 9 indicate that the hydrogenation of the starting material was significantly reduced by the use of either a $H_2$(3%)/Ar mixture or pure argon as a carrier instead of hydrogen. Simultaneously, however, the activity of the catalyst decreased considerably. Another alternative for obtaining a lower degree of hydrogenation is to use a metal less active in the aforesaid reaction. Thus, catalysts containing Rh on silica instead of Pt on silica were investigated.

Comparative Example 10

A Rh/$SiO_2$ catalyst was prepared by impregnating a commercial Grace 432 silica support as follows [H. Arakawa, K. Takeuchi, T. Matsuzaki and Y. Sugi, Chem. Lett. (1984) 1607–1610]:

The Davison grade #57 silica, 16–32 mesh, was evacuated at 200° C. for 2 hours, and impregnated with an aqueous solution of $RhCl_3$.$3H_2O$. The catalyst was dried at 120° C. for 3 hours in a rotary evaporator.

Then, the experimental procedure was carried out as in Comparative Example 1, except for the use of Rh/SiO$_2$ instead of Pt/BaKL. The results are shown in Table 3.

Comparative Example 11

This example was carried out as Comparative Example 10, except for the use of H$_2$ (3%)/Ar mixture as a carrier gas instead of hydrogen. The results are shown in Table 3.

Comparative Example 12

Comparative Example 12 was carried out as Comparative Example 10, except for the use of argon as a carrier gas instead of hydrogen. The results are shown in Table 3.

Comparative Example 13

A Rh/SiO$_2$ catalyst was prepared by impregnating Rh$_4$(CO)$_{12}$ on a commercial Grace 432 silica support to obtain a well dispersed catalyst [J. Kiviaho, VTT Publications 290, Espoo, 1996]. The method of preparation was as follows:

The Grace 432 silica support was dried under vacuum at 600° C. for 2 h to dehydroxylate the surface. 0.9 mmol of the commercially available Rh$_4$(CO)$_{12}$ (Strem Chemicals) was loaded on 1 g of the support from nitrogenated dichloromethane solution under deoxygenated atmosphere. The catalyst was dried slowly in vacuum at room temperature.

Then, the experimental procedure was carried out as in Comparative Example 1, except for the use of the aforesaid Rh/SiO$_2$ instead of the commercial Cr$_2$O$_3$/Al$_2$O$_3$. The results are shown in Table 3.

Comparative Example 14

Comparative Example 14 was carried out as Comparative Example 13, except for the use of the H$_2$ (3%)/Ar mixture instead of hydrogen. The results are shown in Table 3.

EXAMPLES

Examples 1 to 6 illustrate the use of activated carbon as such as a catalyst for the dehydrocyclization reaction. Examples 7 and 8 examine the properties of a completely novel kind of catalyst comprising chromium on carbon. Finally, Examples 9 to 19 describe the preparation of various supported catalysts comprising a non-acidic carbon support.

Example 1

A commercial Takega Shirasagi activated carbon support (particle size 0.3–0.8 mm) was washed with distilled water and dried.

Then, the experimental procedure was carried out as in Comparative Example 2, except for the use of activated carbon instead of commercial Cr$_2$O$_3$/Al$_2$O$_3$. The results are shown in Table 4.

Example 2

A commercial Norit Rox activated carbon support (particle size 0.3–0.8 mm)was washed with distilled water and dried.

Then, the experimental procedure was carried out as in Comparative Example 2, except for the use of activated carbon instead of commercial Cr$_2$O$_3$/Al$_2$O$_3$. The results are shown in Table 4.

Example 3

A commercial activated carbon support (particle size 0.3–0.8 mm) from Johnson & Matthey was washed with distilled water and dried.

Then, the experimental procedure was carried out as in Comparative Example 2, except for the use of activated carbon instead of commercial Cr$_2$O$_3$/Al$_2$O$_3$. The results are shown in Table 4.

The results (Table 4) for the Examples 1–3 very surprisingly indicate that the support alone exhibits high activity for the reaction of 1-(p-tolyl)-2-me-butene. The conversion for activated carbon supports were surprisingly similar, although the carbons exhibit different characteristics, and impregnated catalysts behaved differently. In regard to the formation of 2,6-DMN, the selectivity of all AC supports were similar.

Example 4

Since the performance of the activated carbon is detrimentally influenced by its acidic nature, it can be improved by decreasing the acidity. The simplest way to decrease the acidity of the activated carbon is to thermally decompose the surface groups responsible for it. Thus, an example was carried out after pretreating the AC supports at elevated temperature.

The commercial Takega Shirasagi activated carbon support (particle size 0.3–0.8 mm) was washed with distilled water, dried and pretreated in nitrogen at 800° C. for 2 hours [M. Halttunen, Lic. Thesis, Helsinki University of Technology, Espoo, 1997].

Then, the experimental procedure was carried out as in Comparative Example 2, except for the use of the aforesaid pretreated AC(T) instead of the commercial Cr$_2$O$_3$/Al$_2$O$_3$. The results are shown in Table 4.

Example 5

The commercial Norit Rox activated carbon support (particle size 0.3–0.8 mm) was washed with distilled water, dried and pretreated in nitrogen at 800° C. for 2 hours [M. Halttunen, Lic. Thesis, Helsinki University of Technology, Espoo, 1997].

Then, the experimental procedure was carried out as in Comparative Example 2, except for the use of the aforesaid pretreated AC(N) instead of the commercial Cr$_2$O$_3$/Al$_2$O$_3$. The results are shown in Table 4.

Example 6

The commercial activated carbon support from Johnson & Matthey (particle size 0.3–0.8 mm) was washed with distilled water, dried and pretreated in nitrogen at 800° C. for 2 hours [M. Halttunen, Lic. Thesis, Helsinki University of Technology, Espoo, 1997].

Then, the experimental procedure was carried out as in Comparative Example 2, except for the use of the aforesaid pretreated AC(J&M) instead of the commercial Cr$_2$O$_3$/Al$_2$O$_3$. The results are shown in Table 4.

The results (Table 4) for the Examples 4–6 indicate that the pretreated support exhibited similar overall high activity for the reaction of 1-(p-tolyl)-2-me-butene as the support of Example 11. In regard to the formation of 2,6-DMN, the selectivity of the pretreated AC(T) support was significantly better than that of the non-treated AC(T) support, whereas the activity and selectivity of the pretreated AC(N) was similar to that of the non-treated one. In case of C(C) a slight increase in the selectivity of 2,6-DMN was observed after pretreatment. Thus, the high temperature pretreatment did eliminate acid sites from the surface, and the effect was most pronounced for the originally acidic AC(T) and less profound for the originally neutral AC(N) and basic AC(J&M) material

Examples 7 and 8

The above examples show that the carbon support exhibits preferential characteristics for the reaction. The following example examines the properties of a novel supported catalyst comprising chromium deposited on carbon.

Since the surface of the AC(T) is acidic it has more surface active centres able to adsorb $Cr^{3+}$ ions and thus $Cr(NO_3)_3 \cdot 9H_2O$ may well be used as a precursor salt [C. Moreno-Castilla, F. Carrasco-Marin and J. Rivera-Utrilla, Fuel, 69 (1990) 354–361]. The carbon support may be impregnated using water or ethanol as a solvent. In addition, during the impregnation process the adsorption of cations is favoured if the pH of the solution is higher than the pH of the aqueous slurry of the support [M. C. Román-Martinez, D. Cazorla-Amorós, A. Linares-Solano, H. Yamashita and M. Anpo, Carbon, 33 (1) (1995), 3–13]. The surface of AC(N) is neutral, but nevertheless the same procedure was chosen for catalyst preparation.

Since the amounts of chromium used in the classical $Cr/Al_2O_3$ catalysts have been approx. 15%, the chromium content of the present Cr/C was chosen as 10 wt-%. 5 g of C(T) or C(N) was weighed in to a flask, and it was vacuumed for 1 h. The flask was placed on ice-bath, and the support was impregnated with a solution composed of 2.5 ml of water and 4.272 g of $Cr(NO_3)_2 \cdot 9H_2O$, i.e., the metal loading of the catalyst is approx. 10 wt-% (5 g of support and 0.556 g Cr, that is 0.556:5.556=10 wt-%). The impregnated support was allowed to rest for 3 h, and thereafter the solvent was evaporated at 60° C. under vacuum, and the catalyst was dried in on oven at 110° C. overnight. The catalyst was calcined by elevating the temperature to 500° C. (7° C./min) under nitrogen flow. The calcined catalyst was dried in vacuum for 1 h, placed in an ice-bath and impregnated with a solution composed of 2.5 ml of water and 0.4418 g $K_2CO_3$, that is 0.25 g K (5 wt-%). The catalyst was allowed to rest for 3 hours, and thereafter the solvent was evaporated at 60° C. under vacuum, and the catalyst was dried in on oven at 110° C. overnight. The catalyst was calcined at 500° C. (7° C./min) under nitrogen flow for 1 h.

Then, the experimental procedure was carried out as in Comparative Example 2, except for the use of the aforesaid K—Cr/AC(T) and K—Cr/AC(N) instead of the commercial $Cr_2O_3/Al_2O_3$. The results are shown in Table 5.

The results (Table 5) for the Examples 7 and 8 indicate that the K—Cr/AC(T) catalyst was initially highly active, and the activity of the K—Cr/AC(N) was as in the Comparative Example 4 for K—Cr/Al$_2$O$_3$.

The other means for improving the performance of the activated carbon matrix are evident for the man in the art in the light of the previous patent examples. It is also possible to impregnate the AC support by any other metal suitable for the reaction, such as for example platinum or palladium.

Example 9

A Rh/AC(T) catalyst was prepared by impregnating the commercial Takeda Shirasagi activated carbon (particle size 0.3–0.8 mm) as follows [M. Halttunen, Lic. Thesis, Helsinki University of Technology, Espoo, 1997]:

The support was dried in vacuum at 1–4 mbar and 200° C. for 2 h, and subjected to prewetting with ethanol before impregnation. The support was impregnated to incipient wetness with an aqueous solution of $Rh(NO_3)_3$ to obtain a metal loading of 5 wt-%. The catalyst was dried for 12 h in air at 120° C. and calcined at 400° C. (1° C./min) under nitrogen flow.

Then the experimental procedure was carried out as in Comparative Example 2, except for the use of the aforesaid Rh/AC(T) catalyst instead of commercial $Cr_2O_3/Al_2O_3$. The results are shown in Table 6.

Example 10

A Rh/AC(N) catalyst was prepared by impregnating the commercial Norit Rox activated carbon (particle size 0.3–0.8 mm) as follows [M. Halttunen, Lic. Thesis, Helsinki University of Technology, Espoo, 1997]:

The support was dried in vacuum at 1–4 mbar and 200° C. for 2 h, and subjected to prewetting with ethanol before impregnation. The support was impregnated to incipient wetness with an aqueous solution of $Rh(NO_3)_3$ to obtain a metal loading of 5 wt-%. The catalyst was dried for 12 h in air at 120° C. and calcined at 400° C. (1° C./min) under nitrogen flow.

Then the experimental procedure was carried out as in Comparative Example 2, except for the use of the aforesaid Rh/AC(N) catalyst instead of commercial $Cr_2O3/Al_2O_3$. The results are shown in Table 6.

Example 11

A Rh/AC(J&M) catalyst was prepared by impregnating the commercial coconut based activated carbon (particle size 0.3–0.8 mm) from Johnson & Matthey as follows [M. Halttunen, Lic. Thesis, Helsinki University of Technology, Espoo, 1997]:

The support was dried in vacuum at 1–4 mbar and 200° C. for 2 h, and prewet with ethanol before impregnation. The support was impregnated to incipient wetness with an aqueous solution of $Rh(NO_3)_3$ to obtain a metal loading of 5 wt-%. The catalyst was dried for 12 h in air at 120° C. and calcined at 400° C. (1° C./min) under nitrogen flow.

Then the experimental procedure was carried out as in Comparative Example 2, except for the use of the aforesaid Rh/AC (J&M) catalyst instead of commercial $Cr_2O_3/Al_2O_3$. The results are shown in Table 6.

Example 12

Example 12 was carried out as Example 9, except for the use of the $H_2$ (3%)/$N_2$ mixture instead of a $H_2$ (3%)/Ar mixture. The results are shown in Table 6.

The results (Table 6) for the Examples 9–12 indicate that the rhodium catalysts supported on activated carbon were extremely active in dehydrocyclisation, and the activity decreased in the order Rh/AC(T)>Rh/AC(N)>Rh/AC (J&M). The lower activity of Rh/AC(J&M) was most likely due to the microporous structure of the AC(J&M) support. Namely, the fraction of meso and macropores (2 nm<$d_{pore}$<50 nm and $d_{pore}$>50 nm) was only 5% (out of 0.41 cm$^3$/g) for AC(J&M) whereas it was 15% (out of 0.56 cm$^3$/g) for AC(T) and 30% (out of 0.46 cm$^3$/g) for AC(N), the remaining part being micropores with a diameter below 2 nm. It is evident that the mass transfer of the reactants as well as the reaction of rather large compounds is significantly restricted in such highly microporous material. It is also highly likely that some of the pores of the highly microporous AC(J&M) were blocked by rhodium species whereas the more mesoporous AC(T) and AC(N) were better able to retain their pores open [M. Halttunen, Lic. Thesis, Helsinki University of Technology, Espoo, 1997]. Yet another reason for the better activity of the Rh/AC(T) might lie in its better dispersion; according to TEM the particle size of rhodium was 2–6 nm, and the species were evenly distributed. On Rh/AC(N) and Rh/AC(C), however, particles of 1–10 nm and 4–10 nm together with aggregated sites were present.

However, the selectivities for all carbon supported catalysts were lower than for the best Rh/SiO$_2$. Apparently, the acidic surface groups of the activated carbon supports [M. Halttunen, Lic. Thesis, Helsinki University of Technology, Espoo, 1997] exerted a detrimental effect on the selectivity, and therefore for the purposes of this invention the aforesaid acidic sites were neutralised by a suitable alkali metal, such as potassium.

Example 13

A K—Rh/AC(T) catalyst was prepared from the Rh/AC(T) catalyst obtained in Example 9 by impregnating it as follows:

1 g of the Rh/AC(T) catalyst was weighed into a flask, and it was vacuumed for 2 h. The catalyst was impregnated with a solution composed of 1 ml of water and 0.025 g of potassium acetate, that is 0.01 g K (1 wt-%). The catalyst was allowed to rest for 2 h, and thereafter it was dried at 110° C.

Then, the experimental procedure was carried out as in Comparative

Example 2, except for the use of K—Rh/AC(T) instead of commercial Cr$_2$O$_3$/Al$_2$O$_3$. The results are shown in Table 6.

Example 14

A K—Rh/AC(N) catalyst was prepared from the Rh/AC(N) catalyst obtained in Example 10 by impregnating it as follows:

1 g of the Rh/AC(N) catalyst was weighed into a flask, and it was vacuumed for 2 h. The catalyst was impregnated with a solution composed of 1 ml of water and 0.025 g of potassium acetate, that is 0.01 g K (1 wt-%). The catalyst was allowed to rest for 2 h, and thereafter it was dried at 110° C.

Then, the experimental procedure was carried out as in Comparative Example 2, except for the use of K—Rh/AC(N) instead of commercial Cr$_2$O$_3$/Al$_2$O$_3$. The results are shown in Table 6.

Example 15

A K—Rh/AC(J&M) catalyst was prepared from the Rh/AC(J&M) catalyst obtained in Example 3 by impregnating it as follows:

1 g of the Rh/AC(J&M) catalyst was weighed into a flask, and it was vacuumed for 2 h. The catalyst was impregnated with a solution composed of 1 ml of water and 0.025 g of potassium acetate, that is 0.01 g K (1 wt %). The catalyst was allowed to rest for 2 h, and thereafter it was dried at 110° C.

Then, the experimental procedure was carried out as in Comparative Example 2, except for the use of K—Rh/AC(J&M) instead of commercial Cr$_2$O$_3$/Al$_2$O$_3$. The results are shown in Table 6.

The results (Table 6) for the Examples 13–15 indicate that the activity for the aforesaid promoted catalysts also decreased in order K—Rh/AC(T)>K—Rh/AC(N)>K—Rh/AC(J&M), i.e., in an order similar to the non-promoted catalysts. In addition, both the K—Rh/AC(T) catalyst and the K—Rh/AC(N) catalyst were slightly less active in dehydrocyclisation than their non-promoted counterparts. However, the activity of both the promoted and non-promoted K—Rh/AC(J&M) catalyst was similar most likely due to the limited access of the reactants to the micropores.

In regard to the formation of 2,6-DMN, the selectivity of both the K—Rh/AC(T) catalyst and the K—Rh/AC(N) catalyst were significantly higher than those of their non-promoted counterparts. Apparently, the acidic sites present on the surface of AC(T) (pH=6) and neutral surface of AC(N) (pH=7) were neutralised. Again, however, the performance of the more microporous K—Rh/AC(J&M) catalyst was different from the other two promoted catalysts; the selectivities of the K—Rh/AC(J&M) and Rh/AC(J&M) catalyst were similar most likely due to severe mass transfer limitations. Most likely, the addition of potassium on Rh/AC(J&M) did not effectuate a profound decrease in the acidity of the catalyst, since the surface of AC(J&M) is basic by nature (pH=9)

Since the potassium promotion exerted a beneficial influence on the selectivity of Rh/AC(T) and Rh/AC(N), these two catalysts were also promoted with Ba, since barium is present on the Pt/BaKL catalyst, and with zinc, since zinc ions on the surface of Rh have been found to effectively block the large ensembles of Rh, and thus to result in site isolation of surface Rh [W. M. H. Sachtler and M. Ichikawa, J. Phys. Chem. 90(1986) 4752].

Example 16

A Ba—Rh/AC(T) catalyst was prepared from the Rh/AC(T) catalyst obtained in Example 9 by impregnating it as follows:

1 g of the Rh/AC(T) catalyst was weighed into a flask, and it was vacuumed for 2 h. The catalyst was impregnated with a solution composed of 1 ml of water and 0.038 g barium acetate, that is 0.02 g Ba (2 wt-%). The catalyst was allowed to rest for 2 h, and thereafter it was dried at 110° C.

Then, the experimental procedure was carried out as in Comparative Example 2, except for the use of Ba—Rh/AC(T) instead of commercial Cr$_2$O$_3$/Al$_2$O$_3$. The results are shown in Table 6.

Example 17

A Ba—Rh/AC(N) catalyst was prepared from the Rh/AC(N) catalyst obtained in Example 10 by impregnating it as follows:

1 g of the Rh/AC(N) catalyst was weighed into a flask, and it was vacuumed for 2 h. The catalyst was impregnated with a solution composed of 1 ml of water and 0.038 g barium acetate, that is 0.02 g Ba (2 wt-%). The catalyst was allowed to rest for 2 h, and thereafter it was dried at 110° C.

Then, the experimental procedure was carried out as in Comparative Example 2, except for the use of Ba—Rh/AC(N) instead of commercial Cr$_2$O$_3$/Al$_2$O$_3$. The results are shown in Table 6.

Example 18

A Zn—Rh/AC(T) catalyst was prepared from the Rh/AC(T) catalyst obtained in Example 9 by impregnating it as follows:

1 g of the Rh/AC(T) catalyst was weighed into a flask, and it was vacuumed for 2 h. The catalyst was impregnated with a solution composed of 1 ml of water and 0.0335 g ZnAc$_2$.2H$_2$O, that is 0.01 g Zn (1 wt-%). The catalyst was allowed to rest for 2 h, and thereafter it was dried at 106° C.

Then, the experimental procedure was carried out as in Comparative Example 2, except for the use of Zn—Rh/AC (T) instead of commercial $Cr_2O_3/Al_2O_3$. The results are shown in Table 6.

Example 19

A Zn—Rh/AC(N) catalyst was prepared from the Rh/AC(N) catalyst obtained in Example 10 by impregnating it as follows:

1 g of the Rh/AC(N) catalyst was weighed into a flask, and it was vacuumed for 2 h. The catalyst was impregnated with a solution composed of 1 ml of water and 0.0335 g $ZnAc_2.2H_2O$, that is 0.01 g Zn (1 wt-%). The catalyst was allowed to rest for 2 h, and thereafter it was dried at 106° C.

Then, the experimental procedure was carried out as in Comparative Example 2, except for the use of Zn—Rh/AC(N) instead of commercial $Cr_2O_3/Al_2O_3$. The results are shown in Table 6.

The results (Table 6) for the Examples 16–19 indicate that the activity for the aforesaid promoted catalysts also decreased in order Ba—Rh/AC(T)>Ba—Rh/AC(N) and Zn—Rh/AC(T)>Zn—Rh/AC(N), i.e., in an order similar to the respective non-promoted catalysts and potassium promoted catalysts. In addition, both the Ba and Zn promoted Rh/AC(T) catalyst and the Ba and Zn promoted Rh/AC(N) catalyst were slightly less active in dehydrocyclisation than their non-promoted counterparts. In regard to the formation of 2,6-DMN, the selectivity of both the Ba and Zn promoted Rh/AC(T) catalyst and the Ba or Zn promoted Rh/AC(N) catalyst were significantly higher than those of their non-promoted counterparts.

Thus, all the aforesaid promoters, potassium, barium and zinc, were beneficial in terms of the selectivity of the desired product, 2,6-DMN. Very intriguingly, however, the activities of the catalysts on the aforesaid three activated carbon supports varied considerably indicating that the support itself might play an essential role in the performance of the catalyst. Therefore, their compositions were analysed. The results indicate that the ash content of the AC(T) was significantly lower (0.17%) than for the AC(N) (2.0%) or AC(J&M) (2.1%), i. e., the AC(T) contained less impurities than the other two. Thus, the highest activity of the AC(T) supported catalysts might be due to its mesoporous structure with very low amounts of impurities such as sulphur and chlorine.

TABLE 1

The experimental conditions and results in dehydrocyclisation for Comparative Examples.

| Expt | Catalyst | Recution T, gas, l/h, h | Reaction T ° C. | Carrier gas l/h | Conversion % | 2,6-DMN = (1) Selectivity % | Other DMNs Selectivity % | 1-(p-tolyl)-2-me-butane = (2) Selectivity % | Indenes = (3) M 158 g/mol Selectivity % | (1 + 2)/3 Ratio |
|---|---|---|---|---|---|---|---|---|---|---|
| Comp. 1 | Pt/BaKL | 500° C., $H_2$ 2.0, 2 | 500 | $H_2$ 0.5 | 31 | 23 | 0.5 | 18 | 24 | 1.7 |
| Comp. 2 | $Cr/Al_2O_3$ | 500° C., $H_2$/Ar, 2.0, 2 | 500 | $H_2$/Ar 0.5 | 27 | 33 | 2.1 | 9.4 | 23 | 1.8 |
| Comp. 3 | K—$Cr/Al_2O_3$ | 500° C, $H_2$/Ar, 2.0, 2 | 500 | $H_2$/Ar 0.5 | 13 | 27 | 1.5 | 9.2 | 36 | 1.0 |
| Comp. 4 | K—$Cr/Al_2O_3$ | 500° C., $H_2$/Ar, 2.0, 2 | 500 | $H_2$/Ar 0.5 | 45 | 42 | 1.7 | 12 | 9.5 | 5.7 |
| Comp. 5 | K—$Cr/Al_2O_3$ | 500° C., $H_2$/Ar, 2.0, 2 | 500 | $H_2$/Ar 0.5 | 45 | 28 | 0.8 | — | 5.0 | |
| Comp. 6 | Pt—Cu/NaY | 500° C., $H_2$/Ar, 2.0, 1 | 500 | $H_2$/Ar 0.5 | 50 | 8.2 | 3.0 | 6.1 | 16 | 0.9 |

TABLE 2

The experimental conditions and results in dehydrocyclisation for $Pt/SiO_2$ catalysts.

| Expt | Catalyst | Recution T, gas, l/h, h | Reaction T ° C. | Carrier gas l/h | Conversion % | 2,6-DMN = (1) Selectivity % | Other DMNs Selectivity % | 1-(p-tolyl)-2-me-butane = (2) Selectivity % | Indenes = (3) M 158 g/mol Selectivity % | (1 + 2)/3 Ratio |
|---|---|---|---|---|---|---|---|---|---|---|
| Comp. 7 | 1% $Pt/SiO_2$, 1 g time 2 h | 500° C., $H_2$, 2.0, 2 | 500 | $H_2$, 0.5 | 57 | 23 | 1.6 | 24 | 25 | 1.9 |
| | | | | | 36 | 22 | 1.4 | 18 | 29 | 1.4 |
| Comp. 8 | 1% $Pt/SiO_2$, 1 g time 2 h | 500° C., $H_2$/Ar, 2.0, 2 | 500 | $H_2$/Ar 0.5 | 19 | 26 | 2.4 | 6.5 | 34 | 1.0 |
| | | | | | 13 | 18 | 1.4 | 5.4 | 30 | 0.8 |
| Comp. 9 | 1% $Pt/SiO_2$, 1 g time 2 h | 500° C., $H_2$/Ar, 2.0, 2 | 500 | Ar 0.5 | 19 | 25 | 2.9 | 7.7 | 30 | 1.1 |
| | | | | | 14 | 17 | 2.0 | 6.8 | 30 | 0.8 |

TABLE 3

The experimental conditions and results in dehydrocyclisation for Examples utilizing Rh/SiO₂ catalysts.

| Expt | Catalyst | Reduction T, gas, l/h, h | Reaction T °C. | Carrier gas l/h | Conversion % | 2,6-DMN = (1) Selectivity % | Other DMNs Selectivity % | 1-(p-tolyl)-2-me-butane = (2) Selectivity % | Indenes = (3) M 158 g/mol Selectivity % | (1 + 2)/3 Ratio |
|---|---|---|---|---|---|---|---|---|---|---|
| Comp. 10 | 5% Rh/SiO₂ | 500° C., 2.0, 2 | 500 | H₂ 0.5 | 41 | 23 | 1.3 | 8.5 | 30 | 1.1 |
| Comp. 11 | 5% Rh/SiO₂ | 500° C., H₂/Ar, 2.0, 2 | 500 | H₂/Ar 0.5 | 16 | 42 | 1.9 | 4.6 | 28 | 1.7 |
| Comp. 12 | 5% Rh/SiO₂ | 400° C., H₂, 2.0, 2 | 500 | Ar 0.5 | 32 | 31 | 1.7 | 15 | 21 | 2.2 |
| Comp. 13 | Rh/SiO₂ | 500° C., H₂ 2.0, 1.5 | 500 | H₂ 0.5 | 38 | 27 | 1.5 | 12 | 25 | 1.6 |
| Comp. 14 | Rh/SiO₂ | 400° C., H₂/Ar, 2.0, 1.5 | 500 | H₂/Ar 0.5 | 36 | 43 | 3.1 | 6.9 | 22 | 3.0 |

TABLE 4

The experimental conditions and results in dehydrocyclisation for Examples 1–6 utilizing active carbon support.

| Expt | Catalyst | Reduction T, gas, l/h, h | Reaction T °C. | Carrier gas l/h | Conversion % | 2,6-DMN = (1) Selectivity % | Other DMNs Selectivity % | 1-(p-tolyl)-2-me-butane = (2) Selectivity % | Indenes = (3) M 158 g/mol Selectivity % | (1 + 2)/3 Ratio |
|---|---|---|---|---|---|---|---|---|---|---|
| 1 | AC(T) | 500° C., H₂/Ar, 2.0, 2 | 500 | H₂ Ar 0.5 | 98 | 12 | 1.0 | 6 | 8 | 2.3 |
| 2 | AC(N) | 500° C., H₂/Ar, 2.0, 2 | 500 | H₂/Ar 0.5 | 98 | 17 | 1.5 | 15 | 8 | 4.0 |
| 3 | AC(J&M) | 500° C., H₂/Ar, 2.0, 1 | 500 | H₂/Ar 0.5 | 98 | 15 | 0.3 | 15 | 7 | 4.3 |
| 4 | AC(T) pretreat. 800° C. | 500° C., H₂/Ar, 2.0, 2 | 500 | H₂/Ar 0.5 | 97 | 30 | 2.0 | 12 | 14 | 3.1 |
| 5 | AC(N) pretreat. 800° C. | 500° C., H₂/Ar, 2.0, 2 | 500 | H₂/Ar 0.5 | 98 | 16 | 1.1 | 13 | 10 | 2.9 |
| 6 | AC(J&M) pretreat. 800° C. | 500° C., H₂/Ar, 2.0, 1 | 500 | H₂/Ar 0.5 | 98 | 19 | 0.4 | 11 | 7 | 4.3 |

TABLE 5

The experimental conditions and results in dehydrocyclisation for Examples 18–19 utilizing Cr on active carbon support

| Expt | Catalyst | Reduction T, gas, l/h, h | Reaction T °C. | Carrier gas l/h | Conversion % | 2,6-DMN = (1) Selectivity % | Other DMNs Selectivity % | Hydrogenation Selectivity % | Indenes = (3) M 158 g/mol Selectivity % | (1 + 2)/3 Ratio |
|---|---|---|---|---|---|---|---|---|---|---|
| 7 | Cr/AC(T) time 2 h | 500° C., H₂/Ar, 2.0, 1 | 500 | H₂/Ar 0.5 | 90 | 21 | 0 | 5.0 | 4.5 | 5.8 |
|   |   |   |   |   | 24 | 36 | 0 | 13 | 17 | 2.9 |
| 8 | Cr/AC(N) time 2 h | 500° C., H₂/Ar, 2.0, 1 | 500 | H₂/Ar 0.5 | 45 | 42 | 1.4 | 12 | 11 | 4.9 |
|   |   |   |   |   | 21 | 33 | 0 | 18 | 20 | 2.6 |

TABLE 6

The experimental conditions and results in dehydrocyclisation for Examples 1–11 utilizing Rh on active carbon support.

| Expt | Catalyst | Reduction T, gas, l/h, h | Reaction T °C. | Carrier gas l/h | Conversion % | 2,6-DMN = (1) Selectivity % | Other DMNs Selectivity % | 1-(p-tolyl)-2-me-butane = (2) Selectivity % | Indenes = (3) M 158 g/mol Selectivity % | (1 + 2)/3 Ratio |
|---|---|---|---|---|---|---|---|---|---|---|
| 9 | 0.9% Rh/AC(T) | 500° C., H₂/Ar, 2.0, 1 | 500 | H₂/Ar 0.5 | 96 | 13 | 0.8 | 11 | 8 | 3 |
| 10 | 1.1% Rh/AC(N) | 500° C., H₂/Ar, 2.0, 1 | 500 | H₂/Ar 0.5 | 60 | 29 | 1.8 | 20 | 17 | 2.9 |
| 11 | 1.43% Rh/AC (J&M) | 500° C., H₂/Ar, 2.0, 1 | 500 | H₂/Ar 0.5 | 38 | 34 | 1.8 | 17 | 14 | 3.6 |
| 12 | 0.9% Rh/AC(T) | 500° C., H₂/N₂, 2.0, 1.5 | 500 | H₂/N₂ 0.5 | 95 | 40 | 1.5 | 13 | 13 | 4.1 |
| 13 | 1% K on Rh/AC(T) | 500° C., H₂/Ar, 2.0, 1.5 | 500 | H₂/Ar 0.5 | 81 | 29 | 0.9 | 13 | 15.6 time 1.5 h | 2.7 |

TABLE 6-continued

The experimental conditions and results in dehydrocyclisation for Examples 1–11 utilizing Rh on active carbon support.

| Expt | Catalyst | Reduction T, gas, l/h, h | Reaction T ° C. | Carrier gas l/h | Conversion % | 2,6-DMN = (1) Selectivity % | Other DMNs Selectivity % | 1-(p-tolyl)-2-me-butane = (2) Selectivity % | Indenes = (3) M 158 g/mol Selectivity % | (1 + 2)/3 Ratio |
|---|---|---|---|---|---|---|---|---|---|---|
| 14 | 1% K on Rh/AC(N) | 500° C., $H_2$/Ar, 2.0, 1.5 | 500 | $H_2$/Ar 0.5 | 58 | 39 | 1.1 | 17 | 12 | 4.7 |
| 15 | 1% K on Rh/AC(J&M) | 500° C., $H_2$/Ar, 2.0, 1.5 | 500 | $H_2$/Ar 0.5 | 33 | 32 | 1.1 | 17 | 13 | 3.8 |
| 16 | 2% Ba on Rh/AC(T) | 500° C., $H_2$/Ar, 2.0, 1.5 | 500 | $H_2$/Ar 0.5 | 85 | 25 | 1.5 | 21 | 10 | 4.6 |
| 17 | 2% Ba on Rh/AC/N) | 500° C., $H_2$/Ar, 2.0, 2 | 500 | $H_2$/Ar 0.5 | 66 | 27 | 0.9 | 23 | 12 | 4.2 |
| 18 | 1% Zn on Rh/AC(T) | 500° C., $H_2$/Ar, 2.0, 2 | 500 | $H_2$/Ar 0.5 | 85 | 27 | 1.5 | 12 | 10 | 3.9 |
| 19 | 1% Zn on Rh/AC(N) | 500° C., $H_2$/Ar, 2.0, 2 | 500 | $H_2$/Ar 0.5 | 54 | 30 | 1.5 | 12 | 15 | 2.8 |

What is claimed is:

1. A process for producing 2,6-dimethylnapthalene comprising: subjecting 1-(p-tolyl)-2-methylbutane, 1-(p-tolyl)-2-methylbutene or a mixture thereof to a dehydrocyclization reaction in the presence of a catalyst wherein the catalyst is a non-acidic activated carbon to convert 1-(p-tolyl)-2-methylbutane, 1-(p-tolyl)-2-methylbutene or a mixture thereof to 2,6-dimethylnapthalene.

2. A process of claim 1, wherein the catalyst is a Group VIII noble metal supported on activated carbon.

3. The process of claim 2, wherein the noble metal is selected from the group consisting of rhodium, platinum, and palladium.

4. The process of claim 1, wherein the activated carbon has been neutralized.

5. The process of claim 1, wherein the catalyst is activated carbon modified with a metal other than rhodium.

6. The process of claim 1 wherein the catalyst has been neutralized by a metal of Group 1 to 4 and/or Group 11 to 13.

7. The process of claim 6, wherein the catalyst has been neutralized by using K, Mg, Ca, Ba, Zr, Cu, Zn, Cd and/or B.

8. The process of claim 2, wherein the catalyst has been reduced by a reducing gas.

9. The process of claim 8, wherein the reducing gas is $H_2$ and/or CO.

10. The process of claim 8, wherein the reducing gas is used in the carrier gas as such or together with an inert gas.

11. The process of claim 10, wherein the inert gas is Ar and/or $N_2$.

12. The process of claim 1, wherein a $H_2$/Ar mixture is used for increasing the 2,6-dimethylnapthalene selectivity and for decreasing the hydrogenation selectivity and/or the indanes and indenes selectivity.

13. The process of claim 1, wherein the activated carbon has been pretreated at a high temperature.

14. The process of claim 1, wherein 1-(p-tolyl)-2-methylbutene is subjected to dehydrocyclization.

15. The process of claim 1, wherein the temperature is below 550° C.

16. The process of claim 1, wherein the reaction contact time is below 3 s.

* * * * *